US011555069B2

(12) United States Patent
Okahara et al.

(10) Patent No.: US 11,555,069 B2
(45) Date of Patent: Jan. 17, 2023

(54) COGNITIVE FUNCTION IMPROVING AGENT

(71) Applicant: Kao Corporation, Tokyo (JP)

(72) Inventors: Fumiaki Okahara, Utsunomiya (JP); Yoshitaka Koga, Utsunomiya (JP); Takuya Mori, Utsunomiya (JP)

(73) Assignee: Kao Corporation, Tokyo (JP)

(*) Notice: Subject to any disclaimer, the term of this patent is extended or adjusted under 35 U.S.C. 154(b) by 805 days.

(21) Appl. No.: 16/471,718

(22) PCT Filed: Dec. 26, 2017

(86) PCT No.: PCT/JP2017/046525
§ 371 (c)(1),
(2) Date: Jun. 20, 2019

(87) PCT Pub. No.: WO2018/124010
PCT Pub. Date: Jul. 5, 2018

(65) Prior Publication Data
US 2019/0330333 A1 Oct. 31, 2019

(30) Foreign Application Priority Data
Dec. 26, 2016 (JP) .............................. JP2016-251778

(51) Int. Cl.
*C07K 16/26* (2006.01)
*A61K 31/166* (2006.01)
(Continued)

(52) U.S. Cl.
CPC .............. *C07K 16/26* (2013.01); *A61K 31/166* (2013.01); *A61K 31/201* (2013.01);
(Continued)

(58) Field of Classification Search
CPC .......... A61K 2039/505; A61K 2039/54; A61K 2039/545; A61K 31/166; A61K 31/175;
(Continued)

(56) References Cited

U.S. PATENT DOCUMENTS

2003/0157107 A1  8/2003  Miyawaki et al.
2005/0159415 A1  7/2005  Tsubamoto et al.
(Continued)

FOREIGN PATENT DOCUMENTS

EP    1 506 777 A1    2/2005
JP    2006-342084 A   12/2006
(Continued)

OTHER PUBLICATIONS

The extended European search report, including the supplementary European search report and the European search opinion, for EP Appl. No. 17886842.8, dated Sep. 18, 2020.
(Continued)

*Primary Examiner* — Savitha M Rao
(74) *Attorney, Agent, or Firm* — Sterne, Kessler, Goldstein & Fox P.L.L.C.

(57) ABSTRACT

Provided are a cognitive function improving agent effective for improving cognitive function such as memory and learning ability, and a method for evaluating or selecting the cognitive function improving agent. The cognitive function improving agent comprises a GIP function inhibitor as an active ingredient.

12 Claims, 8 Drawing Sheets

Specification includes a Sequence Listing.

(51) Int. Cl.
  *A61K 31/201* (2006.01)
  *A61K 31/215* (2006.01)
  *A61K 31/404* (2006.01)
  *A61K 31/519* (2006.01)
  *A61K 31/683* (2006.01)
  *A61K 31/717* (2006.01)
  *A61K 31/718* (2006.01)
  *A61K 31/722* (2006.01)
  *A61K 31/734* (2006.01)
  *A61K 31/785* (2006.01)
  *A61K 36/07* (2006.01)
  *A61K 36/185* (2006.01)

(52) U.S. Cl.
  CPC .......... *A61K 31/215* (2013.01); *A61K 31/404* (2013.01); *A61K 31/519* (2013.01); *A61K 31/683* (2013.01); *A61K 31/717* (2013.01); *A61K 31/718* (2013.01); *A61K 31/722* (2013.01); *A61K 31/734* (2013.01); *A61K 31/785* (2013.01); *A61K 36/07* (2013.01); *A61K 36/185* (2013.01)

(58) Field of Classification Search
  CPC .. A61K 31/192; A61K 31/201; A61K 31/202; A61K 31/215; A61K 31/404; A61K 31/506; A61K 31/519; A61K 31/661; A61K 31/683; A61K 31/717; A61K 31/718; A61K 31/722; A61K 31/734; A61K 31/785; A61K 36/07; A61K 36/185; A61K 36/73; A61K 36/899; A61P 25/28; A61P 43/00; C07K 16/26; G01N 2500/00
  See application file for complete search history.

(56) References Cited

U.S. PATENT DOCUMENTS

| 2010/0204106 A1 | 8/2010 | Flatt et al. |
| 2017/0369569 A1 | 12/2017 | Fukuoka et al. |

FOREIGN PATENT DOCUMENTS

| JP | 2010-538030 A | 12/2010 |
| JP | 2013-138638 A | 7/2013 |
| WO | WO 03/097031 A1 | 11/2003 |
| WO | WO 2016/104439 A1 | 6/2016 |

OTHER PUBLICATIONS

Kim, E. et al., "The memory-enhancing effect of erucic acid on scopolamine-induced cognitive impairment in mice." Pharmacol Biochem Behav. Mar. 2016;142:85-90. doi: 10.1016/j.pbb.2016.01.006. Epub Jan. 15, 2016.

Nyberg J et al., "Immunohistochemical distribution of glucose-dependent insulinotropic polypeptide in the adult rat brain." J Neurosci Res. Aug. 1, 2007;85(10):2099-119. doi: 10.1002/jnr.21349. PMTD: 17510976.

International Search Report (ISR) for PCT/JP2017/046525; I.A. fd Dec. 26, 2017, dated Apr. 10, 2018 from the Japan Patent Office, Tokyo, Japan.

International Preliminary Report on Patentability (IPRP), Chapter I of the Patent Cooperation Treaty, including the Written Opinion for PCT/JP2017/046525; I.A. fd Dec. 26, 2017, dated Jul. 2, 2019, by the International Bureau of WIPO, Geneva, Switzerland.

Miyawaki, K et al., "Inhibition of gastric inhibitory polypeptide signaling prevents obesity," Nat Med. Jul. 2002;8(7):738-42. Epub Jun. 17, 2002.

Thangthaeng, N et al., "Daily supplementation with mushroom (*Agaricus bisporus*) improves balance and working memory in aged rats," Nutr Res. Dec. 2015;35(12):1079-84. doi: 10.1016/j.nutres.2015.09.012. Epub Oct. 5, 2015.

Mahmoud, MG et al., "Therapeutic potential and structural elucidation of a water-soluble polysaccharide of a wild edible mushroom *Agaricus bisporus* against neurodegenerative disease, Alzheimer," World Journal of Pharmaceutical Sciences (Oct. 2014), 2(10): 1136-1145, ISSN 0014-2999.

Bennett, L et al., "Vitamin D2-enriched button mushroom (*Agaricus bisporus*) improves memory in both wild type and APPswe/PS1dE9 transgenic mice," PLoS One. Oct. 18, 2013;8(10):e76362. doi: 10.1371/journal.pone.0076362. eCollection 2013, 17 pages.

Faivre, E et al., "Effects of acute and chronic administration of GIP analogues on cognition, synaptic plasticity and neurogenesis in mice," Eur J Pharmacol. Jan. 15, 2012;674(2-3):294-306. doi: 10.1016/j.ejphar.2011.11.007. Epub Nov. 12, 2011.

Rahman, MA et al., "Interpretation of mushroom as a common therapeutic agent for Alzheimer's disease and cardiovascular diseases," Crit Rev Biotechnol. Dec. 2016;36(6):1131-1142. Epub Oct. 22, 2015.

COGNITIVE FUNCTION IMPROVING AGENT

REFERENCE TO SEQUENCE LISTING SUBMITTED ELECTRONICALLY

The content of the electronically submitted substitute sequence listing, file name 2537 1760001_Seqlisting_ST25.txt, size 6741 bytes; and date of creation Aug. 24, 2022, filed herewith, is incorporated herein by reference in its entirety.

FIELD OF THE INVENTION

The present invention relates to a cognitive function improving agent.

BACKGROUND OF THE INVENTION

In recent years, the ratio of the elderly to the total population has increased, and a decrease in memory and learning ability with aging and, further, an increase in dementia as a disease have become problems. Examples of the primary disease of dementia include degenerative brain diseases such as Alzheimer's disease, cerebrovascular disorders caused by cerebral infarction, cerebral hemorrhage, etc., brain tumors, head injury, infectious diseases, and metabolic diseases. In particular, the number of Alzheimer's disease patients is significantly increasing with the progress of aging. Alzheimer's disease causes, for example, a sudden decrease in short-term memory retention, a decrease in memory, and personality disorder and is therefore a social problem from the viewpoint of nursing care.

Alzheimer's disease involves, for example, atrophy and loss of brain tissue and causes a decrease in a neurotransmitter, acetylcholine. Although the pathogenic mechanism has not been revealed yet, it has been reported that senile plaques and neurofibrillary tangles appear in the cerebral cortex and hippocampus, and studies are being conducted from both aspects of amyloid β protein present in the center of senile plaques and tau protein which is a component protein of neurofibrillary tangles.

Conventionally, acetylcholinesterase inhibitors are used for treating dementia and Alzheimer's dementia but do not fundamentally treat dementia, and it is still difficult to say that the inhibitors have sufficient effects.

GIP (gastric inhibitory polypeptide or glucose-dependent insulinotropic polypeptide) is a gastrointestinal hormones belonging to the glucagon/secretin family. GIP is called incretin, as with GLP-1 (glucagon-like peptide 1), and is secreted by K cells present in the small intestine upon intake of lipids or carbohydrates.

GIP is known to promote insulin secretion from pancreatic β cells and to enhance the uptake of glucose into fat cells in the presence of insulin. Accordingly, the action of GIP is considered to be partly responsible for obesity. It has been reported that obesity is actually suppressed by inhibiting the functions of GIP (Non Patent Literature 1).

Furthermore, it has been reported that GIP is partly responsible for insulin resistance (Non Patent Literature 1). When insulin resistance occurs, glucose-absorbing effects mediated by insulin are reduced, and as a result, causing hyperinsulinemia. Hyperinsulinemia is recognized to be a primary cause leading to occurrence of various lifestyle-related diseases including obesity, and prevention and improvement of insulin resistance are important also from the aspect of reducing the risk of lifestyle-related diseases.

However, there is no report that GIP has a relation with cognitive function, and it is not known at all that cognitive function can be improved by decreasing the blood GIP concentration.

(Non Patent Literature 1) Miyawaki K., et al., Nat. Med. 8(7): 738-42, 2002

SUMMARY OF THE INVENTION

The present invention relates to the following aspects 1) to 6):

1) a cognitive function improving agent comprising a GIP function inhibitor as an active ingredient;
2) use of a GIP function inhibitor for producing a cognitive function improving agent;
3) a GIP function inhibitor for use in improvement of cognitive function;
4) use of a GIP function inhibitor for improving cognitive function;
5) a method for improving cognitive function, comprising administering a GIP function inhibitor to a subject in need thereof; and
6) a method for evaluating or selecting a cognitive function improving agent, comprising the following steps:
   (I) measuring GIP function inhibitory activity of test substances;
   (II) evaluating the GIP function inhibitory activity of the test substances based on the results of (I); and
   (III) evaluating or selecting a test substance that increases or enhances GIP function inhibitory activity as a cognitive function improving agent.

DETAILED DESCRIPTION OF THE INVENTION

Figure 1:
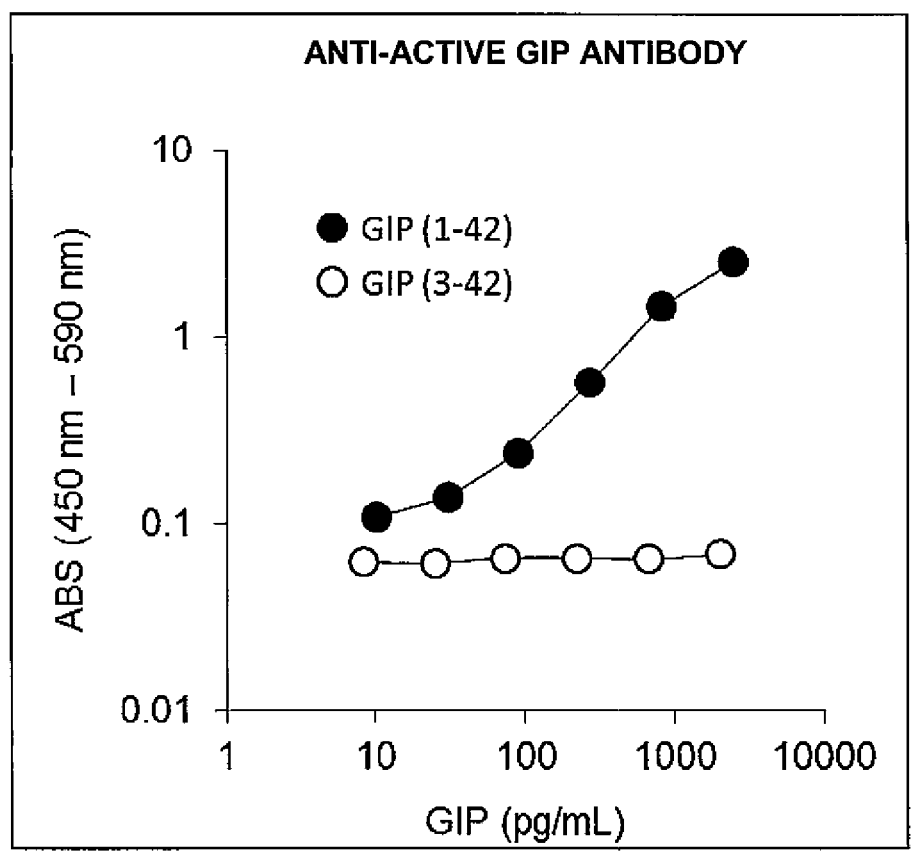
FIG. 1 is a calibration curve for a sandwich ELISA using an anti-active GIP antibody.

The present invention relates to provision of a cognitive function improving agent effective for improving cognitive function such as memory and learning ability and a method for evaluating or selecting a cognitive function improving agent.

The present inventors examined the relationship between GIP and cognitive function and found that short- and long-term memory ability or learning ability is decreased by administration of GIP, the cognitive function can be improved by suppressing the GIP function, and a cognitive function improving agent can be screened by evaluating GIP function inhibitory activity.

The cognitive function improving agent of the present invention can effectively improve impairments with a decrease in cognitive function such as memory of the brain or learning ability.

In the present invention, GIP (gastric inhibitory polypeptide or glucose-dependent insulinotropic polypeptide) is a polypeptide consisting of 42 amino acids. GIP(1-42) has physiological activity (active GIP), but becomes inactive GIP(3-42) by cleavage of two amino acids at the N-terminus with dipeptidyl peptidase-4 (DPP-4) present in vivo.

In the present invention, the "GIP function inhibitor" means a substance that inhibits or suppresses the function of GIP as a gastrointestinal hormone, i.e., a substance that inhibits the function at the GIP gene or GIP receptor gene level or at the GIP itself or GIP receptor level. Specifically, the inhibitor is, for example, an anti-GIP antibody, a GIP receptor antagonist, or a GIP secretion or increase-suppressing agent.

In the present invention, the "anti-GIP antibody" may be any antibody that at least inhibits the function of active GIP and may be a polyclonal antibody or a monoclonal antibody and preferably an antibody that substantially does not bind to inactive GIP (referred to as "anti-active GIP antibody") described in International Publication No. WO 2016/104439 and JP-A-2013-138638. The binding constant (Ka) with active GIP is preferably $10^7$ $M^{-1}$ or more, more preferably $10^8$ $M^{-1}$ or more, even more preferably $10^9$ $M^{-1}$ or more.

The anti-active GIP antibody include antibodies in which the amount of a test antibody bound to inactive GIP is 10% or less at most, preferably 5% or less, more preferably 1% or less, even more preferably 0.1% when the amount of the test antibody bound to active GIP is assumed to be 100%. The amount of the test antibody bound to inactive GIP can be determined by measuring the binding between the test antibody and inactive GIP through a method such as western blotting, immunoprecipitation, immunohistochemical staining, or ELISA.

The anti-active GIP antibody is, for example, an antibody recognizing the 8th and subsequent amino acids from the N-terminus of active GIP (SEQ ID NO: 5) and is preferably an antibody recognizing one or more amino acids selected from at least the 8th to 10th amino acids (SDY).

The anti-active GIP antibody is preferably an antibody further including a region consisting of the amino acid sequence represented by the following formula (1) or a conservative sequence modification thereof in an H-chain:

(1)

EMNPSDGRTHFNE. (SEQ ID NO: 6)

The alphabetical letters in formula (1) mean the one-letter codes of amino acids, and the sequence is shown in order from the N-terminus to the C-terminus. Here, F is phenylalanine, T is threonine, D is aspartic acid, E is glutamic acid, M is methionine, N is asparagine, P is proline, S is serine, G is glycine, R is arginine, and H is histidine.

In the present specification, the "conservative sequence modification" is an amino acid modification in a region other than the complementarity determining region (CDR) participating in antigen determination, and means amino acid modification that does not significantly affect or change the reactivity of the antibody consisting of the unmodified amino acid sequence. Such conservative sequence modification encompasses substitution, addition, and deletion of one to several, preferably 1 to 3, more preferably one amino acid. The conservatively modified amino acid sequence has, for example, a sequence identity of 90% or more, preferably 95% or more, even more preferably 99% or more with the unmodified amino acid sequence. The modification can be introduced into the antibody of the present invention by a standard technique known in the art, such as site-directed mutagenesis or PCR-mediated mutagenesis. Examples of the conservative amino acid substitution include substitution of an amino acid residue with an amino acid residue having a similar side chain (a family of the amino acid residue). Such families of amino acid residues are defined in the art and include amino acids having basic side chains (e.g., lysine, arginine, and histidine), acid side chains (e.g., aspartic acid and glutamic acid), uncharged polar side chains (e.g., glycine, asparagine, glutamine, serine, threonine, tyrosine, cysteine, and tryptophan), nonpolar side chains (e.g., alanine, valine, leucine, isoleucine, proline, phenylalanine, and methionine), β-branched side chains (e.g., threonine, valine, and isoleucine), and aromatic side chains (e.g., tyrosine, phenylalanine, tryptophan, and histidine).

The amino acid sequence represented by formula (1) described above encodes the region consisting of 13 amino acid residues at the 50th to 62nd positions of the amino acid sequence represented by SEQ ID NO: 2 representing an H-chain variable region.

Accordingly, the anti-active GIP antibody more preferably includes a region consisting of the amino acid sequence represented by SEQ ID NO: 2 or a conservative sequence modification thereof as the H-chain variable region. Furthermore, the anti-active GIP antibody more preferably includes a region consisting of the amino acid sequence represented by SEQ ID NO: 2 or a conservative sequence modification thereof as the H-chain variable region and a region consisting of the amino acid sequence represented by SEQ ID: 4 or a conservative sequence modification thereof as the L-chain variable region.

Examples of the anti-active GIP antibody including a region consisting of the amino acid sequence represented by SEQ ID NO: 2 as the H-chain variable region and a region consisting of the amino acid sequence represented by SEQ ID NO: 4 as the L-chain variable region include the monoclonal antibody produced by hybridoma 9B9H5-B9 line shown in Production Example 1 described later.

The anti-GIP antibody of the present invention may be a fragment of the antibody such as F(ab')$_2$, F(ab'), single chain Fv (scFv), disulfide-linked Fv (dsFv) in which amino acid residues substituted for the cysteine residues in the VH and the VL are linked to each other through a disulfide bond, or a polymer thereof, or a dimerized V region (Diabody) in which scFv is dimerized as long as the fragment has the reactivity. Furthermore, the fragment of the antibody may be a peptide including a part of the anti-active GIP antibody, as long as the peptide has the reactivity, and specifically includes a peptide including a part of the amino acid sequence constituting the antibody and having the reactivity.

In addition, the immunoglobulin class of the anti-GIP antibody of the present invention is not particularly limited and may be any of IgG, IgM, IgA, IgE, IgD, and IgY immunoglobulin classes and is preferably IgG. The antibody of the present invention encompasses antibodies of any isotype.

In addition, the anti-GIP antibody of the present invention may be any one of antibodies of non-human animals, human chimeric antibodies, humanized antibodies, and human antibodies. Examples of the antibodies of non-human animals include antibodies of mouse, rat, hamster, and guinea pig, and mouse antibodies are preferred.

Here, the "human chimeric antibody" is an antibody modified by genetic engineering such that the constant region of an antibody derived from a non-human animal and specifically binding to GIP is replaced with the corresponding constant region of a human antibody, and is preferably a human-mouse chimeric antibody. The "humanized antibody" is an antibody modified by genetic engineering such that the primary structure except for the H chain and L chain complementarity determining region (CDR) of an antibody derived from a non-human animal and specifically binding to GIP is replaced with the corresponding primary structure of a human antibody. The "human antibody" means a human antibody that is an expression product of a completely human-derived antibody gene.

The anti-GIP antibody that can be used is a monoclonal antibody produced by a known method, in addition to a commercially available polyclonal antibody (Bioss Inc.). Examples of the monoclonal antibody derived from a mammal include those produced by hybridomas and those produced by a well-known genetic engineering technique using a designed antibody gene or antibody fragment gene.

For example, the anti-active GIP antibody described above is produced as a recombinant single-chain antibody protein (scFv) having antigen-binding ability by inserting a DNA encoding an H-chain variable region (e.g., a DNA consisting of the nucleotide sequence represented by SEQ ID NO: 1) and a DNA encoding an L-chain variable region (e.g., a DNA consisting of the nucleotide sequence represented by SEQ ID NO: 3) into the downstream of a promoter in respective appropriate vectors to construct recombinant vectors, introducing the recombinant vectors into host cells to produce an H-chain and an L-chain from the resultant transformants, and linking the chains via a possible peptide; or by linking a DNA encoding an H-chain variable region (e.g., a DNA consisting of the nucleotide sequence represented by SEQ ID NO: 1) and a DNA encoding an L-chain variable region (e.g., a DNA consisting of the nucleotide sequence represented by SEQ ID NO: 3) via a DNA encoding a known linker, inserting the resultant DNA construct into the downstream of a promoter in an appropriate vector to construct a recombinant vector and expressing the DNA sequence in a host cell (see, for example, MacCfferty, J., et al., Nature, 348, 552-554, 1990; and Tim Clackson, et al., Nature, 352, 642-628, 1991). Furthermore, the anti-active GIP antibody may be produced by linking a DNA encoding a variable region and a DNA encoding a constant region and expressing the DNA sequence. In this case, the constant region and the variable region may be derived from the same antibody or may be derived from a different antibody.

As described above, an amino acid mutation for preparing functionally equivalent polypeptides can be introduced by, for example, site-directed mutagenesis.

An anti-active GIP antibody-producing hybridoma can be basically produced by a known technique as follows.

For example, active GIP or a peptide including an N-terminal amino acid sequence (a peptide consisting of the 1st to 15th amino acids of SEQ ID NO: 5) is linked to an appropriate carrier protein, for example, keyhole limpet hemocyanin (KLH) or bovine serum albumin, as needed, to enhance the immunogenicity and is used for immunization of a non-human mammal to produce the hybridoma. The active GIP or the peptide used as the sensitizing antigen (immunogen) can be produced by genetic engineering or chemical synthesis.

The mammal to be immunized with the sensitizing antigen is not particularly limited, is preferably selected considering the compatibility with myeloma cells of a mammal as a parent cell to be used for cell fusion and is usually a rodent such as a mouse, a rat, or a hamster.

An animal is immunized with the sensitizing antigen according to a known method. For example, the sensitizing antigen is injected intraperitoneally or subcutaneously into a mammal for immunization. Specifically, the sensitizing antigen is diluted or suspended in, for example, PBS (phosphate-buffered saline) or physiological saline to obtain an appropriate amount, the dilution or suspension is, if desired, mixed with an appropriate amount of a common adjuvant, for example, Freund's complete adjuvant for emulsification. The emulsion is then administered subcutaneously, intradermally, or intraperitoneally to an animal for temporal stimulation, and the same procedure is repeated as needed. The amount of the antigen administered is appropriately determined according to the administration route and the animal species and, usually, is preferably about from 10 µg to 1 mg per once. After confirmation of an increase in the level of the desired antibody in the serum of the animal thus immunized, immunocytes are taken from the mammal having an increased antibody level and are used for cell fusion. In particular, examples of the immunocyte preferred for the cell fusion include a spleen cell.

As myeloma cells of the mammal serving as the other parent cell to be fused with the immunocytes, various known cell lines, such as P3X63, NS-1, MPC-11, and SP2/0, are appropriately used.

The immunocytes and the myeloma cells can be fused according to a known method, for example, a Kohler's method (Kohler, et al., Nature, vol. 256, p 495-497 (1975)). That is, the immunocytes and the myeloma cells are mixed in the presence of a cell fusion promoter such as polyethylene glycol (PEG having an average molecular weight of 1,000 to 6,000, concentration: 30% to 60%) or hemagglutinating virus of Japan (HVJ) in a nutrient medium such as a RPMI1640 medium or a MEM medium, containing an auxiliary such as dimethyl sulfoxide, if desired, to form fused cells (hybridomas).

The hybridomas formed by fusion are cultured in a selection medium, such as a medium containing hypoxanthine, thymidine, and aminopterin (HAT medium), for 1 to 7 days and thereby separated from unfused cells. The resulting hybridomas are subjected to further selection based on a produced antibody (antibody binding to active GIP and not substantially binding to inactive GIP).

The selected hybridomas are cloned according to a known limiting dilution method to establish a monoclonal antibody-producing hybridoma.

A method for detecting the activity of the antibody produced by the hybridoma can be a known method, such as an ELISA, agglutination, or radioimmunoassay.

In order to obtain a monoclonal antibody from the resulting hybridoma, for example, the following methods are adopted: a method which involves culturing the hybridoma according to an ordinary method to obtain the monoclonal antibody as a culture supernatant, or a method which involves administering the hybridoma to a mammal compatible therewith, proliferating the hybridoma, and obtaining the monoclonal antibody as an ascitic fluid thereof.

The antibody can be purified by a known purification method, such as a salting-out method, a gel filtration method, ion exchange chromatography, or affinity chromatography.

In the present invention, examples of the "GIP receptor antagonist" include methylidene hydrazide compounds described in WO 2003/097031, specifically, 4-hydroxybenzoic acid (2-bromobenzylidene) hydrazide, 3-cyano-4-hydroxybenzoic acid [1-(2,3,5,6-tetramethylbenzyl)indol-4-yl]methylidene hydrazide, 3-chloro-4-hydroxybenzoic acid (4-methoxynaphthalen-1-yl)methylidene hydrazide, and 3-chloro-4-hydroxybenzoic acid [1-(5-chlorothiophen-2-ylmethyl)-1H-indol-5-yl]methylidene hydrazide.

In the present invention, examples of the "GIP secretion or increase-suppressing agent" include BMPP (3-bromo-5-methyl-2-phenylpyrazolo[1,5-a]pyrimidin-7-ol) (WO 2001/87341), alginic acid (JP-A-2013-166741), phosphatidylethanolamine (JP-A-2010-222284), polyglutamic acid (JP-A-2012-144486), quillaja (JP-A-2012-171914), lysophosphatidylinositol (JP-A-2012-171915), cellulose nanofiber (JP-A-2009-126837), β-chitin nanofiber (JP-A-2010-241713), diacylglycerol (JP-A-2006-342084), hydroxypropylated starch (JP-A-2006-342085), monoacylglycerol (JP-A-2007-290989), a very long chain fatty acid having 20 or more carbon atoms (for example, arachidic acid, behenic acid, lignoceric acid, cerotic acid, montanic acid, melissic acid, lacceric acid, gadoleic acid, dihomo-γ-linolenic acid, erucic acid, docosapentaenoic acid, nervonic acid, hexacosenoic acid, and octacosenoic acid: JP-A-2011-225458), long chain unsaturated fatty acid ethanolamide (for example, oleylethanolamide, linoleylethanolamide, linolenylethanolamide, homo-γ-linolenylethanolamide, arachidonylethanolamide, and 7,10,13,16-docosatetraenylethanolamide: JP-A-2010-180203), a rice bran extract (JP-A-2012-515139), catechins (JP-A-2010-260856), triacylglycerol containing 10 mass or more of α-linolenic acid as a constituent fatty acid (JP-A-2013-075887), acylglycerol with a C14 to C18 saturated fatty acid bound at the 2-position of the glycerol skeleton (for example, 2-acylmonoglycerol with lauric acid (12:0), myristic acid (14:0), palmitic acid (16:0), linoleic acid (18:2), oleic acid (18:1), stearic acid (18:0), or arachidonic acid (20:4) bound at the 2-position: JP-A-2016-047805), and a squeeze or extract of common mushroom (*Agaricus bisporus*) (PCT/JP2017/043101).

As shown in Examples described later, the anti-GIP antibody suppresses a decrease in short- and long-term memory and learning ability caused by administration of GIP in mice and thus has an activity of improving short- and long-term memory and learning ability of aged mice.

Accordingly, a GIP function inhibitor, such as the anti-GIP antibody, can be a cognitive function improving agent and can be used for producing a cognitive function improving agent.

In addition, the GIP function inhibitor can be used for improving cognitive function. Here, the use can be a use for a human being or a non-human animal or in a sample derived therefrom, and may be a therapeutic use or a non-therapeutic use. The term "non-therapeutic" is a concept that does not include medical practice, i.e., a concept not including a method for operation, treatment, or diagnosis for a human being, more specifically, a concept not including a method for performing operation, treatment, or diagnosis for a human being by a doctor or a person instructed by a doctor.

In the present invention, the "cognitive function" means higher functions of the brain including judgement, calculation, understanding, learning, thinking, language, and memory (short-term memory and long-term memory), and the "improvement of cognitive function" means maintenance and improvement of the cognitive function and reducing and healing of various symptoms due to a decrease in the cognitive function.

Accordingly, the cognitive function improving agent of the present invention is useful for preventing or treating a disease or a condition showing impairment of the cognitive function. Examples of the disease or the condition showing cognitive impairment include dementia (examples: senile dementia, Alzheimer's dementia, cerebrovascular dementia, posttraumatic dementia, and dementia caused by various diseases, such as dementia caused by brain tumor, dementia caused by chronic subdural hematoma, dementia caused by normal pressure hydrocephalus, postmeningitic dementia, and Parkinson's dementia), non-demented cognitive impairment (example: mild cognitive impairment (MCI)), and memory or learning impairment (example: memory or learning impairment caused by brain developmental disorder).

The cognitive function improving agent of the present invention can be human or animal medicine showing an effect of improving the cognitive function or a material or preparation to be blended in medicine.

When the cognitive function improving agent of the present invention is used as medicine, the medicine can be administered in an arbitrary dosage form. Examples of the dosage form include oral administration in the form of, for example, tablets, capsules, granules, powders, and syrups, and parenteral administration in the form of, for example, injections, suppositories, inhalants, transdermal absorbents, and external preparations. Preferred form is parenteral administration.

The medicinal preparations of such various dosage forms can be prepared from the GIP function inhibitor of the present invention alone or in appropriate combination with other pharmaceutically acceptable ingredients such as an excipient, a binder, a filler, a disintegrant, a surfactant, a lubricant, a dispersant, a buffering agent, a preservative, a corrective agent, a flavor, a coating agent, a carrier, and a diluent.

The content of the GIP function inhibitor in the cognitive function improving agent of the present invention is preferably 0.001 mass % or more, more preferably 0.01 mass % or more; preferably 10 mass % or less, more preferably 5 mass % or less, even more preferably 1 mass % or less, even more preferably 0.1 mass % or less; and is preferably from 0.001 to 10 mass %, preferably from 0.001 to 5 mass %, preferably from 0.001 to 1 mass %, more preferably from 0.01 to 0.1 mass %.

The amount of the cognitive function improving agent of the present invention administered or taken can vary depending on the condition, weight, sex, age, or other factors of the subject. In the case of oral administration or intake, the amount as the GIP function inhibitor is preferably 1 mg or more, more preferably 5 mg or more and preferably 500 mg or less, more preferably 100 mg or less, more preferably 20 mg or less per day for an adult.

The subject to be administered with the cognitive function improving agent of the present invention is preferably a human being whose memory and learning ability is decreased or a human being who desires to maintain and improve the cognitive function.

The method for evaluating or selecting the cognitive function improving agent of the present invention includes a step (I) of measuring GIP function inhibitory activity of test substances, a step (II) of evaluating the GIP function inhibitory activity of the test substances based on the results of the step (I), and a step (III) of evaluating or selecting a test substance that increases or enhances GIP function inhibitory activity as a cognitive function improving agent.

Here, examples of a method for measuring GIP function inhibitory activity include the following methods.

1) GIP receptor cDNA is introduced into GIP receptor-expressing cells, and cAMP is produced by GIP using the cells in the presence of a test substance. Subsequently, the cAMP is extracted and is measured by immunoassay.

2) GIP receptor cDNA is introduced into GIP receptor-expressing cells, and a gene including a bacterial lac Z gene linked to a cAMP-dependent promoter is introduced into the cells. The cells are reacted with GIP in the presence of a test substance. The activity of β-galactosidase accumulated in the cells according to the cAMP produced by GIP activity is measured.

3) GIP receptor cDNA is introduced into GIP receptor-expressing cells, and a test substance and a radiolabeled GIP are added to the cells. After incubation, the radioactivity is measured.

4) Intestine-derived or neuron-derived cells producing GIP are stimulated with a test substance, and then GIP produced in the cells or culture supernatant is quantitatively measured.

5) The amount of GIP secreted in the presence of a test substance by nutrients, such as lipids and carbohydrates, is measured by ELISA.

Evaluation of the GIP function inhibitory activity of test substances is performed by identifying a test substance that increases or enhances the GIP function inhibitory activity.

For example, the evaluation can be performed by comparing the GIP function inhibitory activities measured when test substances are added at different concentrations. In a more specific example, the GIP function inhibitory activities are compared between a higher concentration of test substance addition group and a lower concentration of test substance addition group; between a test substance addition group and a placebo addition group; or between before and after the addition of a test substance. When the GIP function inhibitory activity is increased or enhanced by addition of a test substance or by addition of a higher concentration of a test substance, the test substance can be identified as a substance that increases or enhances the GIP function inhibitory activity.

The test substance identified as one that increases or enhances the GIP function inhibitory activity is evaluated or selected as a cognitive function improving agent.

The test substance is not particularly limited as long as the test substance is a substance that is desired to be used for improving cognitive function, may be a naturally occurring substance or be a substance artificially synthesized by a chemical or biological method and may be a compound, composition, or mixture.

Regarding the above-described embodiments, in the present invention, the following aspects are further disclosed.

<1> A cognitive function improving agent comprising a GIP function inhibitor as an active ingredient.

<2> Use of a GIP function inhibitor for producing a cognitive function improving agent.

<3> A GIP function inhibitor for use in improvement of cognitive function.

<4> (Non-therapeutic) Use of a GIP function inhibitor for improving cognitive function.

<5> A method for improving cognitive function, comprising administering a GIP function inhibitor to a subject in need thereof.

<6> In aspects <1> to <5>, the GIP function inhibitor is an anti-GIP antibody, a GIP receptor antagonist, or a GIP secretion or increase-suppressing agent.

<7> In aspect <6>, the anti-GIP antibody is preferably: an anti-active GIP antibody.

<8> aspect <6>, the GIP receptor antagonist is preferably 4-hydroxybenzoic acid (2-bromobenzylidene) hydrazide, 3-cyano-4-hydroxybenzoic acid [1-(2,3,5,6-tetramethylbenzyl)indol-4-yl]methylidene hydrazide, 3-chloro-4-hydroxybenzoic acid (4-methoxynaphthalen-1-yl)methylidene hydrazide, or 3-chloro-4-hydroxybenzoic acid [1-(5-chlorothiophen-2-ylmethyl)-1H-indol-5-yl]methylidene hydrazide.

<9> In aspect <6>, the GIP secretion or increase-suppressing agent is preferably a squeeze or extract of common mushroom, 3-bromo-5-methyl-2-phenylpyrazolo[1,5-a]pyrimidin-7-ol, alginic acid, phosphatidylethanolamine, polyglutamic acid, quillaja, lysophosphatidylinositol, cellulose nanofiber, β-chitin nanofiber, diacylglycerol, hydroxypropylated starch, monoacylglycerol, a very long chain fatty acid having 20 or more carbon atoms, long chain unsaturated fatty acid ethanolamide, a rice bran extract, triacylglycerol containing 10 mass % or more of α-linolenic acid as a constituent fatty acid, or acylglycerol with a C14 to C18 saturated fatty acid bound at the 2-position of the glycerol skeleton.

<10> In aspect <7>, the anti-active GIP antibody is preferably an anti-active GIP antibody that binds to active GIP and does not substantially bind to inactive GIP, wherein the antibody at least recognizes one or more amino acids selected from the 8th to 10th amino acids of the amino acid sequence represented by SEQ ID NO: 5, and includes a region consisting of the amino acid sequence represented by the following formula (1) or a conservative sequence modification thereof in an H-chain:

(1)            SEQ ID NO: 6
EMNPSDGRTHFNE.

EMNPSDGRTHFNE (1).

<11> In aspect <10>, the anti-active GIP antibody is preferably an antibody including a region consisting of the amino acid sequence represented by SEQ ID NO: 2 or a conservative sequence modification thereof as an H-chain variable region.

<12> In aspect <11>, in the anti-active GIP antibody, the conservatively modified amino acid sequence preferably has an identity of 90% or more with the amino acid sequence represented by SEQ ID NO: 2.

<13> In aspect <10>, the anti-active GIP antibody is preferably an antibody including a region consisting of the amino acid sequence represented by SEQ ID NO: 2 or a conservative sequence modification thereof as an H-chain variable region and including a region consisting of the amino acid sequence represented by SEQ ID NO: 4 or a conservative sequence modification as an L-chain variable region.

<14> In aspect <13>, in the anti-active GIP antibody, the amino acid sequence obtained by conservative sequence modification of the amino acid sequence represented by SEQ ID NO: 2 has an identity of 90% or more with the amino acid sequence represented by SEQ ID NO: 2, and the amino acid sequence obtained by conservative sequence modification of the amino acid sequence represented by SEQ ID NO: 4 has an identity of 90% or more with the amino acid sequence represented by SEQ ID NO: 4.

<15> A method for evaluating or selecting a cognitive function improving agent, comprising the following steps:

(I) measuring GIP function inhibitory activity of test substances;

(II) evaluating the GIP function inhibitory activity of the test substances based on the results of the step (I); and (III) evaluating or selecting a test substance that increases or enhances GIP function inhibitory activity as a cognitive function improving agent.

<15> The method according to aspect <15>, wherein the GIP function inhibitory activity is measured by introducing GIP receptor cDNA into GIP receptor-expressing cells, producing cAMP by GIP using the cells in the presence of a test substance, subsequently extracting the cAMP, and measuring the cAMP by immunoassay.

EXAMPLES

Production Example 1: Preparation of Anti-Active GIP Antibody (1) Synthesis of Peptide for Immunization Polyethylene glycol was added to N-terminus 15 amino acids of active GIP (GIP(1-15)) (PEGylation (polyethylene glycolation)), and keyhole limpet hemocyanin (KLH) was then chemically bonded thereto to produce KLH-linked PEGylated GIP (1-15) as an immunogen. PEGylated N-terminus 15 amino acids of active GIP (GIP(1-15)) was used as an antigen (1) for measurement, and PEGylated N-terminus 13 amino acids of inactive GIP (GIP(3-15)) was used as an antigen (2) for measurement.

(2) Immunization

BALB/c mice (Oriental Yeast Co., Ltd.) were immunized subcutaneously in the back. In the first immunization, an emulsion prepared by mixing the antigen prepared as above and Freund's complete adjuvant was administered. Booster immunization was performed with an emulsion prepared by mixing the antigen and Freund's incomplete adjuvant every two weeks from the first immunization. The amount of the antigen used in one immunization was in a range of 0.1 to 0.2 mg. Seven weeks after the first immunization, the antibody titer of the serum collected from each mouse was measured to confirm an increase in the antibody titer.

(3) Cell Fusion

The spleen was excised from the mouse with an increased antibody titer to obtain spleen cells. The obtained spleen cells were fused with mouse myeloma cell line P3U1 by a PEG method. Subsequently, the fused cells were seeded in 20 96-well plates ($1 \times 10^5$ cells/well).

(4) Screening

The reaction between the hybridoma culture supernatant and the antigen (1) and (2) for measurement was evaluated by ELISA using immobilized antigen (1) and (2), and hybridomas that are positive for the antigen (1) and negative for the antigen (2) were selected as anti-active GIP monoclonal antibody-producing hybridomas.

(5) Cloning

Antibody-producing hybridoma was cloned by culturing the hybridomas obtained above through a limiting dilution method to obtain single colonies, and single colony-forming wells were subjected to ELISA again to establish 9B9H5-B9 line, which produces an antibody that is positive for the antigen (1) and negative for the antigen (2) (WO 2016/104439).

To preserve the resulting antibody-producing hybridomas, the hybridomas were cultured and collected in the logarithmic growth phase and were then prepared to a cell concentration of $1 \times 10^6$ cells/mL with a cryopreservation liquid containing FBS (fetal bovine serum). The hybridomas were then dispensed into cryogenic tubes at $1 \times 10^6$ cells/tube and were preserved at $-80°$ C. in a Bicell.

(6) Antibody Production

The resulting antibody-producing hybridomas in the cryogenic vial were initiated in a hybridoma-SFM (Serum-Free Medium). After amplifying and culturing the hybridomas, culturing was performed in two roller bottles (500 mL×2, 1 L), and the culture supernatant was collected. The collected culture supernatant was purified to a monoclonal antibody by affinity chromatography using Protein A.

Test Example 1: Reactivity with Active GIP by ELISA

The reactivity between the monoclonal antibody prepared in Production Example 1 and active GIP was confirmed by ELISA. The amino group of the anti-active GIP monoclonal antibody was biotinylated with NH2 group biotinylation kit (manufactured by Dojindo Laboratories). ELISA was performed using the produced biotinylated anti-active GIP monoclonal antibody at 1 μg/mL instead of a detection antibody, GIP detection antibody (biotinylated anti-total GIP monoclonal antibody), included in Human (total) GIP ELISA kit (manufactured by EMD Millipore Corporation). A 4-fold dilution series of GIP(1-42) or GIP(3-42) was prepared in 6 steps (8.2 to 2000 pg/mL) with a 2000 pg/mL solution as the highest concentration. By using an anti-total GIP monoclonal antibody (included in Human GIP (total) ELISA kit manufactured by EMD Millipore Corporation) as a capture antibody, the biotinylated anti-active GIP monoclonal antibody as a detection antibody, and a peroxidase-streptavidin conjugate for detection, sandwich ELISA was conducted to prepare a calibration curve with GIP concentration on the X-axis and 450 nm-590 nm absorbance on the Y-axis (FIG. 1).

As shown in FIG. 1, the absorbance was not increased in GIP(3-42) even in a high-concentration range, and the absorbance was increased only in GIP(1-42) in a concentration-dependent manner. Accordingly, it was confirmed that the monoclonal antibody prepared in Production Example 1 is an antibody which does not show cross-reactivity with GIP(3-42) and be capable of specifically detecting GIP(1-42).

Example 1: Decrease in Memory and Learning Function by GIP and Suppression of Decrease in Memory and Learning Function by Anti-GIP Antibody (1) Animal and Breeding Method Six-week-old leptin receptor deficient C57BLKS/J male mice (db/db mice, Oriental Yeast Co., Ltd.) were transferred (room temperature: $23°$ C., humidity: $55 \pm 10\%$, light period: 7:00 to 19:00) and were fed with food and water ad libitum. The food was CE-2 (CLEA Japan, Inc.), and the mice were acclimated for 2 weeks under the above-mentioned environment and were then used for testing.

(2) Preparation of GIP Solution and GIP-Binding Anti-GIP Antibody Solution by Antigen Antibody Reaction Mouse-derived GIP (manufactured by AnaSpec, Inc.) was dissolved in physiological saline at a concentration of 500 nM to give a GIP solution. Mouse-derived GIP (manufactured by AnaSpec, Inc.) and the anti-active GIP antibody produced in Production Example 1 were dissolved in physiological saline at concentrations of 500 nM and 0.1 mg/mL, respectively, and the resulting solution was incubated for 1 to 2 hours at room temperature to give a GIP-binding anti-GIP antibody solution.

(3) Administration Amount and Administration Method

Physiological saline (control group), the GIP solution (5 nmol/kg body weight) (GIP administration group), or the GIP-binding anti-GIP antibody solution (GIP: 5 nmol/kg body weight, anti-GIP antibody: 1 mg/kg body weight) (GIP+anti-GIP antibody administration group) was intraperitoneally administered to mice (30-week-old) twice a week (9:00 to 10:00 a.m.), 8 times in total. The start date of administration (the first administration) was taken as the first day of the administration, and the 2nd, 3rd, 4th, 5th, 6th, 7th, and 8th administration were, respectively, performed on the 2nd day, 7th day, 8th day, 14th day, 15th day, 20th day, and 21st day. Memory tests (Y-maze test and novel object recognition test) were performed 2 to 3 hours after the administration.

(4) Y-Maze (Short-Term Memory) Test

The test was performed 10 days before the start of the administration and 20 days after the start of the administration (after seven administrations) to measure the short-term memory and learning ability (working memory). Each mouse was placed at an end of a plastic Y-maze (manufactured by Noldus Information Technology) in which the arms each have a length of 40 cm and a height of 12 cm and form an angle of 120° with each other, and the behavior of the mouse was video-recorded for 10 minutes to measure the order and the number of entries into the arms. The score of short-term memory and learning ability was evaluated by the spontaneous alternation behavior change rate (see the following calculation formula). Spontaneous alternation behavior change rate (%)=(number of spontaneous alternation behaviors)/[(total number of entries)−2]×100 (number of spontaneous alternation behaviors: number of entries into the respective arms without overlapping).

(5) Novel Object Recognition (Long-Term Memory) Test

The test was performed 5 days before the start of the administration and 15 days after the start of the administration (after six administrations) to measure the long-term memory and learning ability (reference memory). Each mouse was placed in a box having 30 cm length, 30 cm width, and 40 cm height (manufactured by Noldus Information Technology) and was acclimated for 5 minutes each day for continuous 3 days (from 11th to 13th day from the start of the administration). On the following day, two identical objects (rubber objects wrapped with blue rubber tape: columns each having 4 cm diameter and 3.5 cm height) were placed in the box (at a position with a space of 10 cm in length and 10 cm in width from the wall), and the behavior of the mouse was video-recorded for 5 minutes to measure the number of recognitions (the number of times the mouse approached each object within 1 cm) (training trial, on the 14th day from the start of the administration). Furthermore, on the following day (after 24 hours), the mouse was placed in the box in which one of the two objects was replaced with a novel object having a different shape (a glass object wrapped with red rubber tape: a regular triangular pyramid with a side of 6 cm), and the behavior of the mouse was video-recorded for 5 minutes to measure the number of recognitions (retention trial, on the 15th day from the start of the administration). The score of long-term memory and learning ability was evaluated by the recognition rate of the novel object in the retention trial (see the following calculation formula).

Novel object recognition rate (%)=(number of novel object recognitions)/(total recognitions)×100.

(6) Statistical Analysis

The analysis results were shown as the average value (Ave.)±standard error (SE). The statistical analysis was performed using Bonferroni's post hoc test and Student's t-test, and the difference was judged to be statistically significant when the P value was 0.05 or less.

(7) Results

Figure 2:
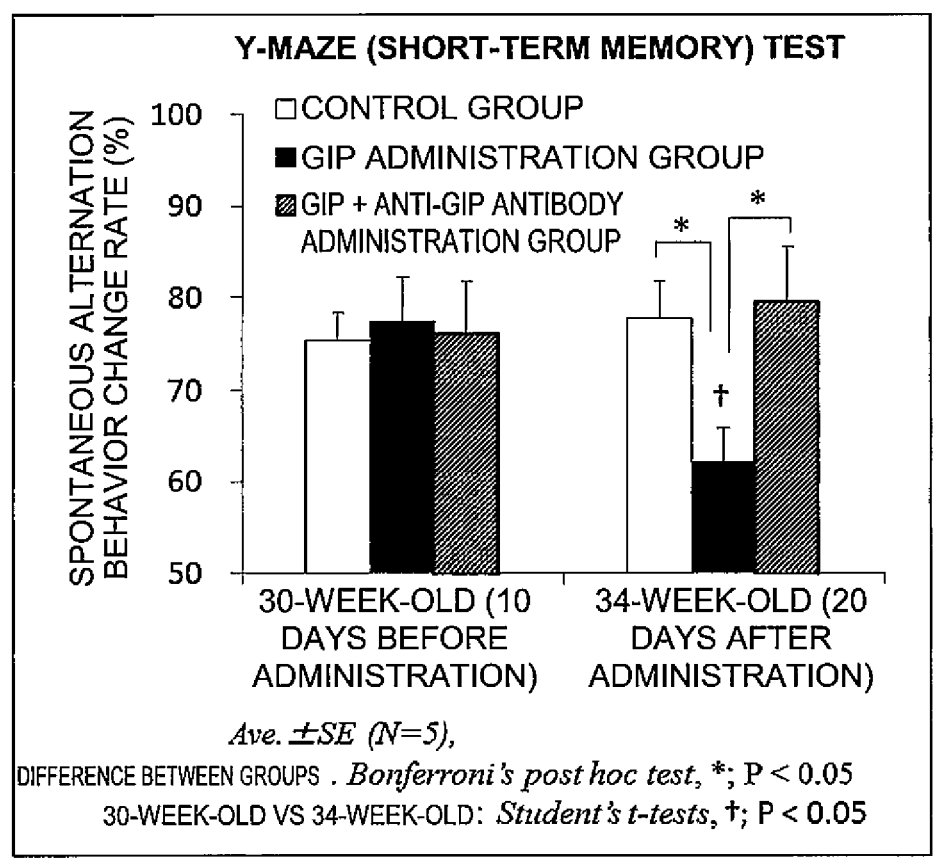
FIG. 2 is a graph showing changes in short-term memory and learning function by continuous administration of GIP or a GIP-binding anti-GIP antibody.
Figure 3:
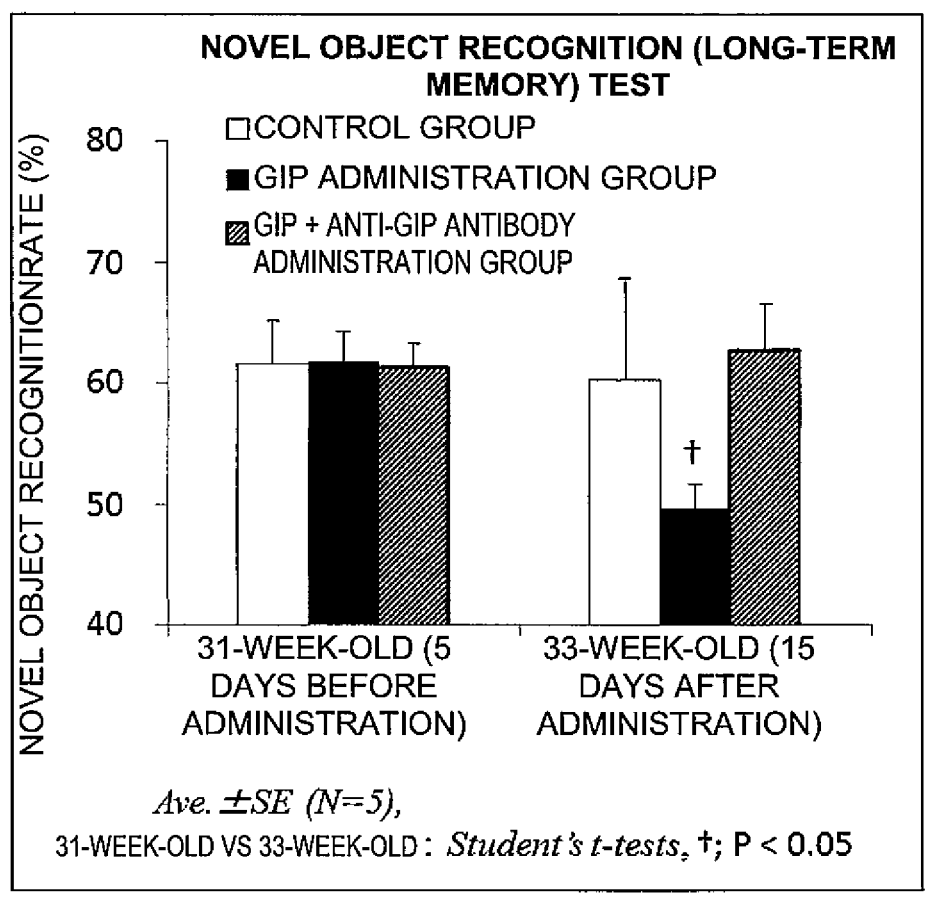
FIG. 3 is a graph showing changes in long-term memory and learning function by continuous administration of GIP or a GIP-binding anti-GIP antibody.

In the Y-maze test, a decrease in the spontaneous alternation behavior change rate (short-term memory and learning ability) was observed in the GIP administration group compared to the non-administration. In the GIP+anti-GIP antibody administration group, a decrease in the short-term memory and learning ability was not observed, while observed in the GIP administration group, and the score was almost the same as that of the control group (FIG. 2). Also, in the novel object recognition test, similarly, a decrease in the novel object recognition rate (long-term memory and learning ability) was observed in the GIP administration group compared to the non-administration. In the GIP+anti-GIP antibody administration group, a decrease in the long-term memory and learning ability was not observed, while observed in the GIP administration group, and the score was almost the same as that of the control group (FIG. 3).

Example 2: Age-Related Change of Blood GIP Level (1) Animal and Breeding Method

Four-week-old C57BL/6J male mice (CLEA Japan, Inc.) were transferred (room temperature: 23° C., humidity: 55±10%, light period: 7:00 to 19:00) and were fed with food and water ad libitum. The mice were acclimated using CE-2 (CLEA Japan, Inc.) as food for 1 week and were then fed with normal diet (D12450K, Research Diets, Inc.) or high fat diet (D12451, Research Diets, Inc.) for 95 weeks.

(2) Blood Collection

Whole blood of each week old mouse (5-, 10-, 15-, 20-, 30-, 40-, 50-, 65-, 80-, and 100-week-old mice) was collected from the abdominal vena cava under isoflurane anesthesia.

(3) Measurement of Blood GIP Level

The collected blood was centrifuged to prepare each plasma fraction, and the blood GIP concentration was then measured according to a usual method with a GIP ELISA kit (manufactured by EMD Millipore Corporation) as the total GIP.

(4) Statistical Analysis

The analysis results were shown as the average value (Ave.)±standard error (SE). The statistical analysis was performed using 2-way ANOVA followed by Bonferroni's post hoc test, and the difference was judged to be statistically significant when the P value was 0.05 or less.

(5) Results

Figure 4:
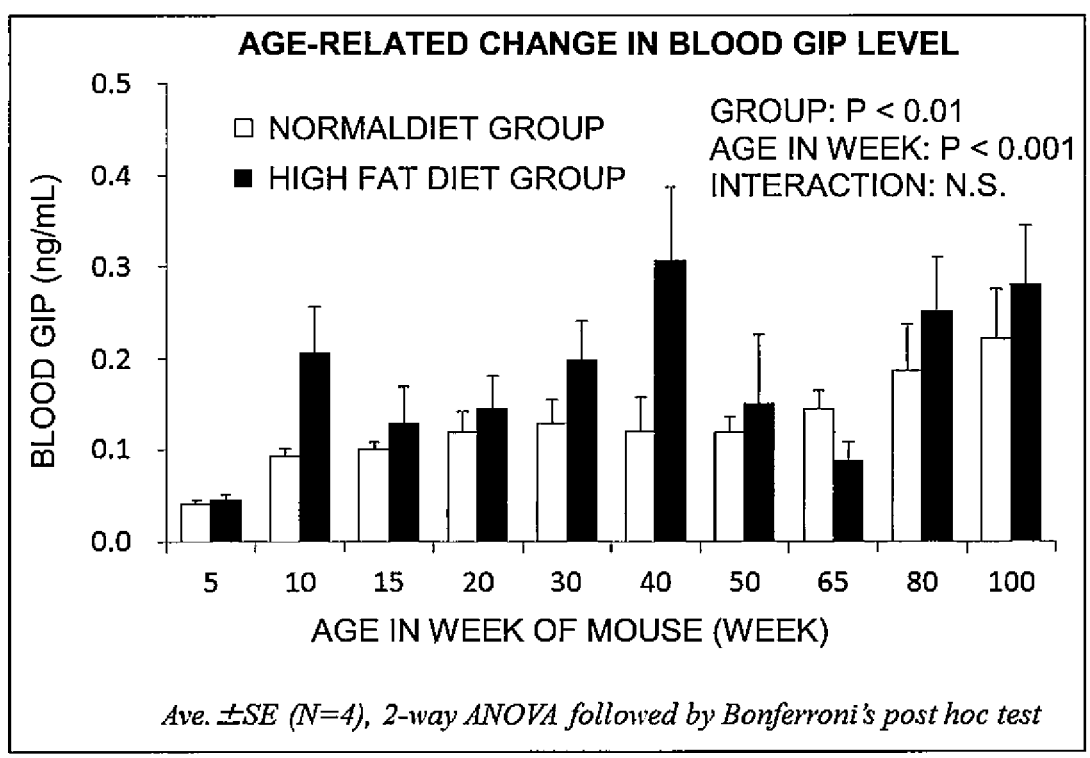
FIG. 4 is a graph showing age-related changes in blood GIP level.

An increase in the blood GIP concentration with aging was observed. In particular, a significant increase in the blood GIP level was observed in the high fat diet group compared to the normal diet group (FIG. 4). Since it is known that the total GIP and the amount of active GIP change in conjunction (WO 2012-121302), it is considered that the amount of active GIP is also increased.

Example 3: Memory and Learning Function-Improving Activity of Anti-GIP Antibody on Aged Mouse (1) Animal and Breeding Method Four-week-old C57BL/6J male mice (CLEA Japan, Inc.) were transferred (room temperature: 23° C., humidity: 55±10%, light period: 7:00 to 19:00) and were fed with food (D12450K, Research Diets, Inc.) and water ad libitum for 111 weeks.

(2) Preparation of Anti-GIP Antibody Solution

The anti-active GIP antibody produced in Production Example 1 was dissolved in physiological saline at a concentration of 0.05 mg/mL to give an anti-GIP antibody solution.

(3) Administration Amount and Administration Method

Physiological saline (control group) or the anti-GIP antibody solution (0.5 mg/kg body weight) (anti-GIP antibody administration group) was intraperitoneally administered to C57BL/6J mice (107-week-old) once a week (9:00 to 10:00 a.m.), 6 times in total.

(4) Y-Maze (Short-Term Memory) Test

The test was performed 1 week before the start of the administration and 1 week after the start of the administration (after two administrations), 3 weeks after the start (after four administrations), and 5 weeks after the start (after six administrations) to measure the short-term memory and learning ability (working memory). Each mouse was placed at an end of a plastic Y-maze (manufactured by Noldus Information Technology) in which the arms each have a length of 40 cm and a height of 12 cm and form an angle of 120° with each other, and the behavior of the mouse was video-recorded for 10 minutes to measure the order and the number of entries into the arms. The score of short-term memory and learning ability was evaluated by the spontaneous alternation behavior change rate (see the following calculation formula). Spontaneous alternation behavior change rate (%)=(number of spontaneous alternation behaviors)/[(total number of entries)−2]×100 (number of spontaneous alternation behaviors: number of entries into the respective arms without overlapping).

(5) Novel Object Recognition (Long-Term Memory) Test

The test was performed 5 weeks after the start of the administration to measure the long-term memory and learning ability (reference memory). Each mouse was placed in a box having 30 cm length, 30 cm width, and 40 cm height (manufactured by Noldus Information Technology) and was acclimated for 5 minutes each day for continuous 3 days. On the following day, two identical objects (rubber objects wrapped with blue rubber tape: columns each having 4 cm diameter and 3.5 cm height) were placed in the box (at a position with a space of 10 cm in length and 10 cm in width from the wall), and the behavior of the mouse was video-recorded for 5 minutes to measure the number of recognitions (the number of times the mouse approached each object within 1 cm) (training trial). Furthermore, on the following day (after 24 hours), the mouse was placed in the box in which one of the two objects was replaced with a novel object having a different shape (a glass object wrapped with red rubber tape: a regular triangular pyramid with a side of 6 cm), and the behavior of the mouse was video-recorded for 5 minutes to measure the number of recognitions (retention trial). The score of long-term memory and learning ability was evaluated by the recognition rate to the novel object in the retention trial (see the following calculation formula).

Novel object recognition rate (%)=(number of novel object recognitions)/(total recognitions)×100

(6) Statistical Analysis

The analysis results were shown as the average value (Ave.)±standard error (SE). The statistical analysis was performed using 2-way ANOVA followed by Bonferroni's post hoc test and Student's t-test, and the difference was judged to be statistically significant when the P value was 0.05 or less.

(7) Results

Figure 5:
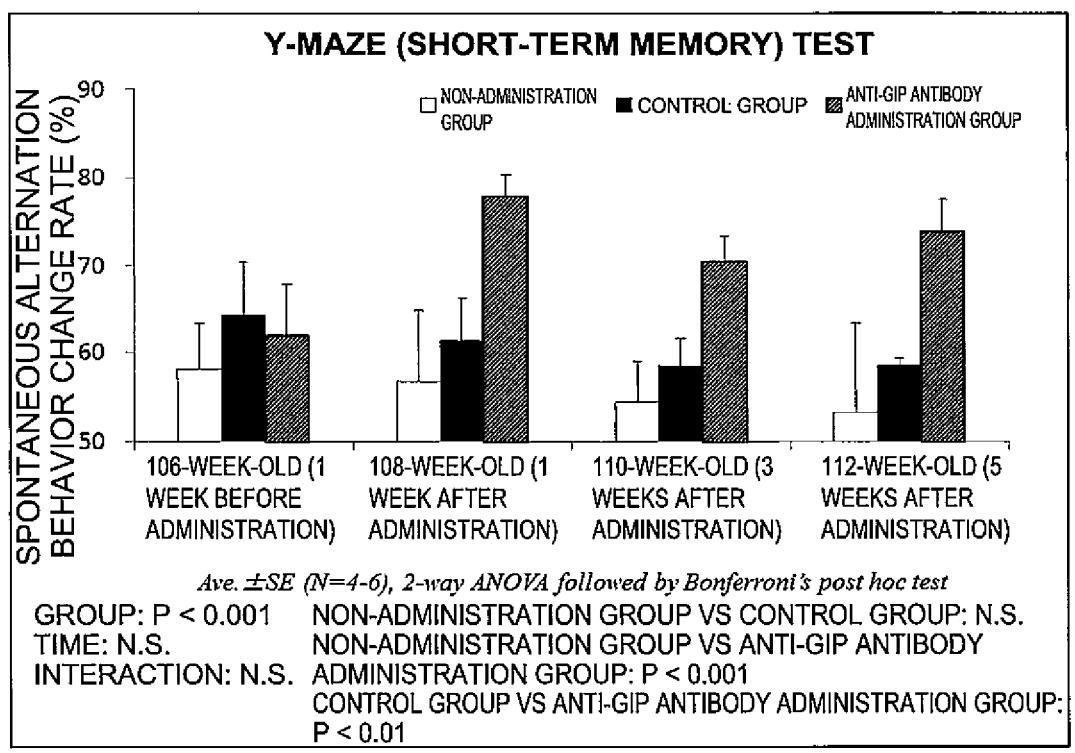
FIG. 5 is a graph showing changes in short-term memory and learning function by continuous administration of an anti-GIP antibody to aged mice.
Figure 6:
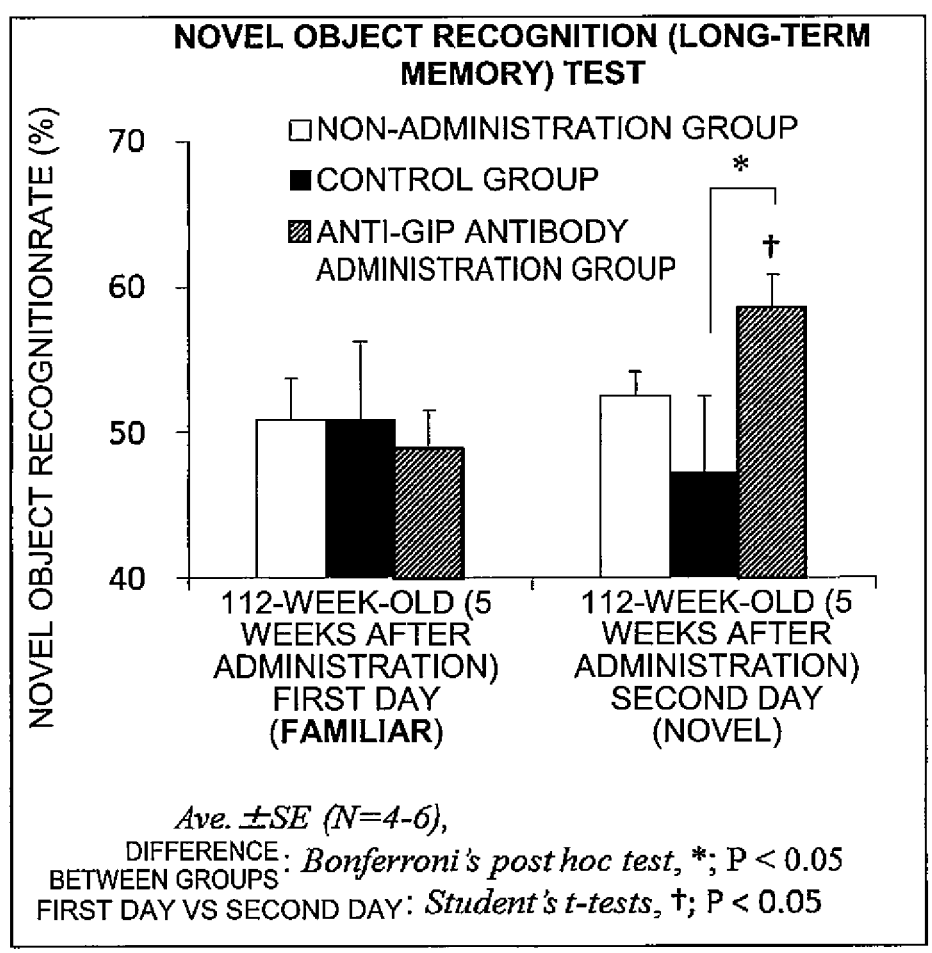
FIG. 6 is a graph showing changes in long-term memory and learning function by continuous administration of an anti-GIP antibody to aged mice.

In the Y-maze test, an increase in the spontaneous alternation behavior change rate (short-term memory and learning ability) was observed in the anti-GIP antibody administration group, compared to the non-administration group and the control group (FIG. 5). Also, in the novel object recognition test, similarly, an increase in the novel object recognition rate (long-term memory and learning ability) was observed in the anti-GIP antibody administration group, compared to the control group (FIG. 6).

Example 4: Memory and Learning Function-Improving Activity of GIP Secretion or Increase-Suppressing Agent on Aged Mouse (1) Animal and Breeding Method Four-week-old C57BL/6J male mice (CLEA Japan, Inc.) were transferred (room temperature: 23° C., humidity: 55±10%, light period: 7:00 to 19:00) and were fed with food and water free libitum. The mice were fed with high fat diet (D12451, Research Diets, Inc.) for 57 weeks (up to 61-week-old) and were then grouped such that the body weights and memory and learning functions of each group were respectively equivalent to each other. The mice were fed with high fat diet containing 30% lipid (high fat diet group) or 30% high fat diet containing 20% common mushroom squeeze (common mushroom intake group) as experimental diet for 15 weeks (76-week-old). During the breeding period, the body weight was measured once a week, and the food intake amount was measured 3 times a week. During the breeding period, the intake of the food and water was free. The memory and learning function was evaluated 1 month (65- to 66-week-old) and 3 months (75- to 76-week old) after the start of the test.

(2) Preparation of Food and Composition Ratio

The fruiting body (11.3 kg) of common mushroom (*Agaricus bisporus*) was squeezed with a slow juicer (HURON Group Corporation) under room temperature conditions and was then lyophilized to prepare a common mushroom squeeze powder (308.2 g). The ingredient composition of the common mushroom squeeze was analyzed by a food composition analytical center. The composition ratio of the common mushroom squeeze is shown in Table 1. The composition ratio of each food used in the test is shown in Table 2. The food containing a common mushroom squeeze was prepared, in consideration of the composition of each ingredient, by replacing ingredients with the common mushroom squeeze such that the nutritional composition and calorie were equivalent to those of the high fat diet as the control.

TABLE 1

Ingredient composition of common mushroom squeeze

| Common mushroom squeeze | g/100 g |
|---|---|
| Carbohydrate | 41.2 |
| Lipid | 2.1 |
| Protein | 34.4 |
| Dietary fiber | 9.4 |
| Ash | 11.4 |
| Moisture | 1.5 |

TABLE 2

Dietary composition of food

| | Control | Common mushroom | Wheat bran |
|---|---|---|---|
| Corn oil | 25 | 24.54 | 23.64 |
| Lard | 5 | 4.96 | 4.90 |
| Pregelatinized potato starch | 28.5 | 19.28 | 11.96 |
| Sucrose | 13 | 12.96 | 12.90 |
| Casein | 20 | 13.08 | 14.23 |
| Cellulose | 4 | 3.02 | 0 |
| Mineral mixture | 3.5 | 1.18 | 1.45 |
| Vitamin mixture | 1 | 0.96 | 0.90 |
| Common mushroom squeeze | 0 | 20 | 0 |
| Steamed wheat bran | 0 | 0 | 30 |

The contents in experimental diet are expressed in percentage (w/w).

(3) Y-Maze (Short-Term Memory) Test

The test was performed before the intake of the experimental diet and 1 month and 3 months after the start of the intake to measure the short-term memory and learning ability (working memory). Each mouse was placed at an end of a plastic Y-maze (manufactured by Noldus Information Technology) in which the arms each have a length of 40 cm and a height of 12 cm and form an angle of 120° with each other, and the behavior of the mouse was video-recorded for 10 minutes to measure the order and the number of entries into the arms. The score of short-term memory and learning ability was evaluated by the spontaneous alternation behavior change rate (see the following calculation formula).

Spontaneous alternation behavior change rate (%)= (number of spontaneous alternation behaviors)/ [(total number of entries)−2]×100.

(number of spontaneous alternation behaviors: number of entries into the respective arms without overlapping).

(4) Novel Object Recognition (Long-Term Memory) Test

The test was performed before the intake of the experimental diet and 1 month and 3 months after the start of the intake to measure the long-term memory and learning ability (reference memory). Each mouse was placed in a box having 30 cm length, 30 cm width, and 40 cm height (manufactured by Noldus Information Technology) and was acclimated for 5 minutes each day for continuous 3 days. On the following day, two identical objects (rubber objects wrapped with blue rubber tape: columns each having 4 cm diameter and 3.5 cm height) were placed in the box (at a position with a space of 10 cm in length and 10 cm in width from the wall), and the behavior of the mouse was video-recorded for 5 minutes to measure the number of recognitions (the number of times the mouse approached each object within 1 cm) (training trial). Furthermore, on the following day (after 24 hours), the mouse was placed in the box in which one of the two objects was replaced with a novel object having a different shape (a glass object wrapped with red rubber tape: a regular triangular pyramid with a side of 6 cm), and the behavior of the mouse was video-recorded for 5 minutes to measure the number of recognitions (retention trial). The score of long-term memory and learning ability was evaluated by the recognition rate to the novel object in the retention trial (see the following calculation formula).

Novel object recognition rate (%)=(number of novel object recognitions)/(total recognitions)×100.

(5) Statistical Analysis

The analysis results were shown as the average value (Ave.)±standard error (SE). The statistical analysis was performed using 2-way ANOVA followed by Dunnett's post hoc test, and the difference was judged to be statistically significant when the P value was 0.05 or less.

(6) Results

Figure 7:
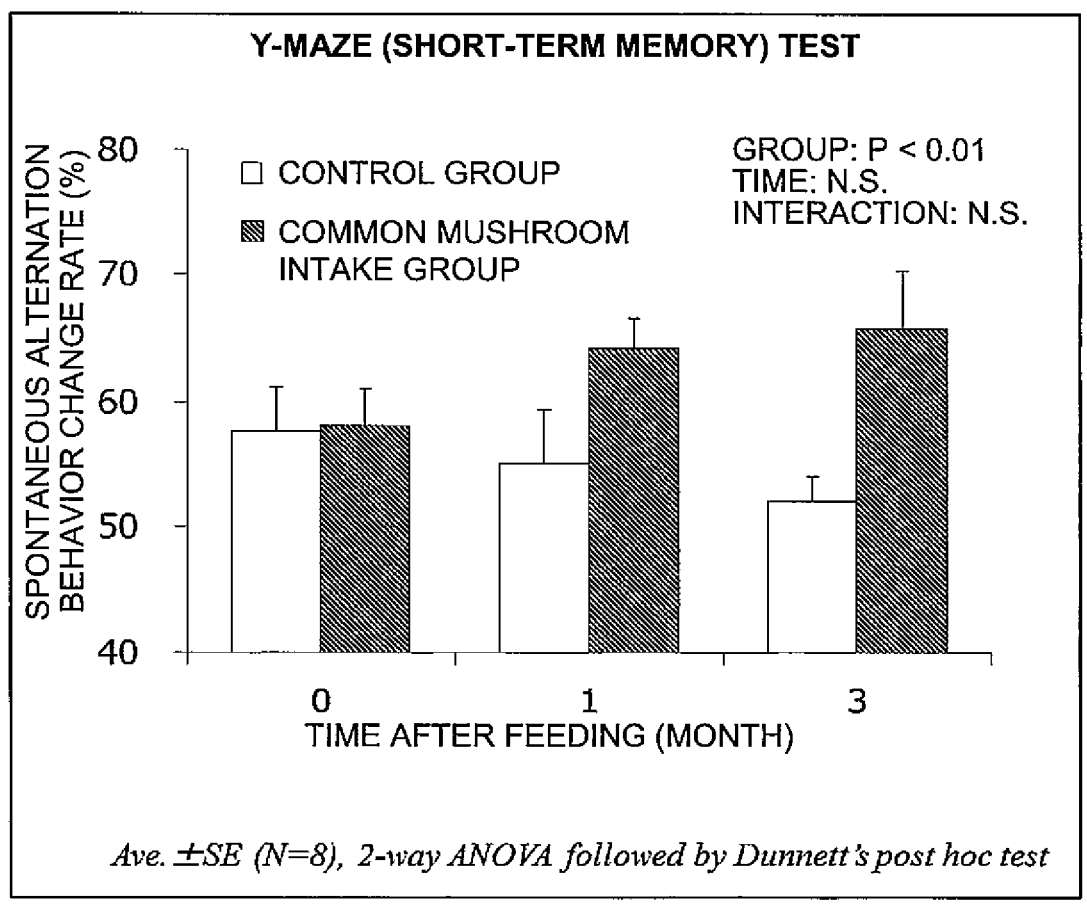
FIG. 7 is a graph showing changes in short-term memory and learning function by continuous intake of a GIP secretion inhibitor by aged mice.
Figure 8:
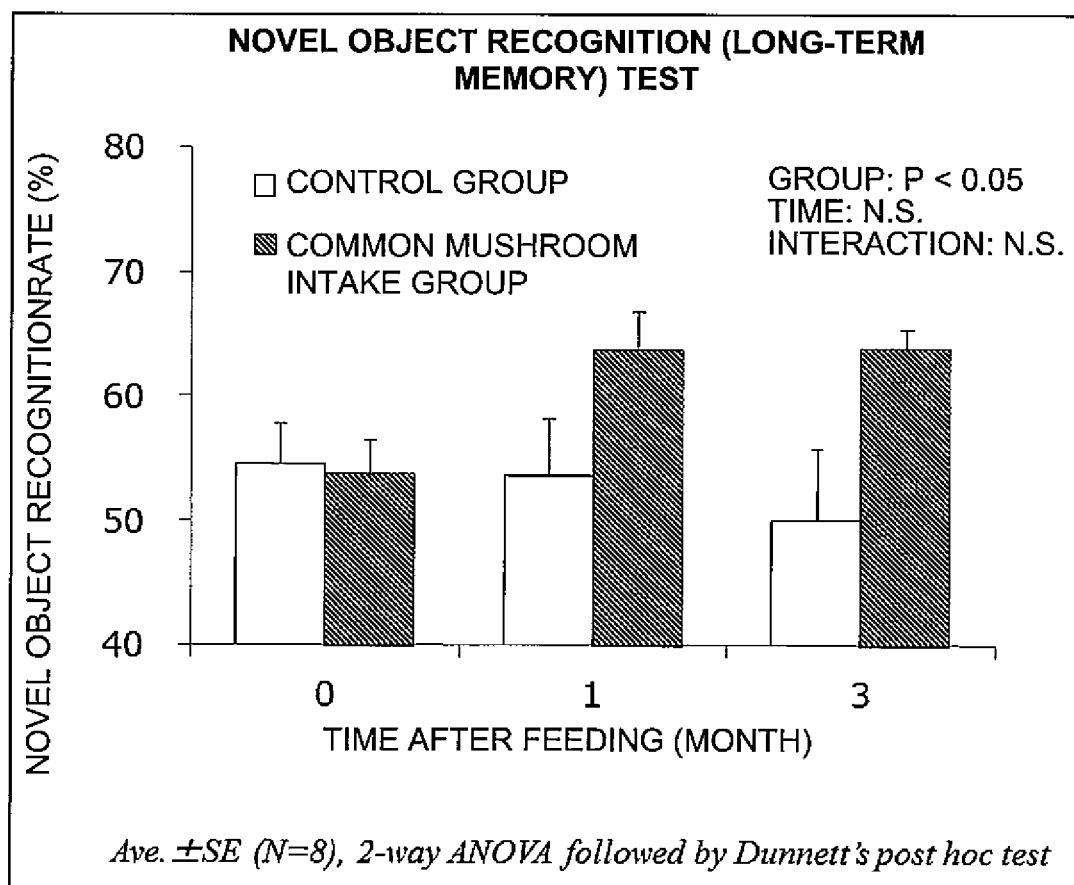
FIG. 8 is a graph showing changes in long-term memory and learning function by continuous intake of a GIP secretion inhibitor by aged mice.

In the Y-maze test, an increase in the spontaneous alternation behavior change rate (short-term memory and learning ability) was observed in the common mushroom (GIP secretion or increase-suppressing agent) intake group compared to the control group (FIG. 7). Also, in the novel object recognition test, similarly, an increase in the novel object recognition rate (long-term memory and learning ability) was observed in the common mushroom (GIP secretion or increase-suppressing agent) intake group compared to the control group (FIG. 8).

The invention claimed is:

1. A method for improving cognitive function of a subject in need thereof, comprising administering a Glucose-Dependent Insulinotropic Polypeptide (GIP) function inhibitor to the subject, thereby improving the subject's cognitive function, wherein the cognitive function that is improved is the subject's memory and wherein the GIP function inhibitor is an anti-GIP antibody.

2. The method according to claim 1, wherein the anti-GIP antibody is an anti-active GIP antibody.

3. The method of claim 2, wherein the anti-active GIP antibody recognizes one or more amino acids selected from the 8th to 10th amino acids of the amino acid sequence of SEQ ID NO: 5, and wherein the antibody includes a region consisting of the amino acid sequence of the following formula (1) or a conservative sequence modification thereof in an H-chain: EMNPSDGRTHFNE (1).

4. The method of claim 3, wherein the antibody includes a region consisting of the amino acid sequence of the following formula (1) in an H-chain:
EMNPSDGRTHFNE (1).

5. The method of claim 2, wherein the amino acid sequence of the anti-active GIP antibody comprises a region consisting of the amino acid sequence of SEQ ID NO:2 or a conservative sequence modification thereof as an H-chain variable region.

6. The method of claim 5, wherein the amino acid sequence of the anti-active GIP antibody comprises a region consisting of the amino acid sequence of SEQ ID NO: 2 as an H-chain variable region.

7. The method of claim 5, wherein the conservatively modified amino acid sequence has a sequence identity of 90% or more with the amino acid sequence of SEQ ID NO: 2.

8. The method of claim 2, wherein the anti-active GIP antibody comprises a region consisting of the amino acid sequence of SEQ ID NO:2 or a conservative sequence modification thereof as an H-chain variable region, and comprises a region consisting of the amino acid sequence of SEQ ID NO: 4 or a conservative sequence modification thereof as an L-chain variable region.

9. The method of claim 8, wherein the amino acid sequence of the anti-active GIP antibody comprises the amino acid sequence of SEQ ID NO: 2 as an H-chain variable region and comprises the amino acid sequence of SEQ ID NO: 4 as an L-chain variable region.

10. The method of claim 8, wherein the amino acid sequence of the region consisting of an amino acid sequence that is a conservative sequence modification of SEQ ID NO:2 has 90% or more sequence identity to SEQ ID NO:2 as an H-chain variable region and wherein the amino acid sequence of the region consisting of the amino acid sequence that is a conservative sequence modification of SEQ ID NO: 4 has 90% or more sequence identity to SEQ ID NO:4 as an L-chain variable region.

11. The method of claim 2, wherein the subject is in need of improvement in the subject's short term memory.

12. The method of claim 2, wherein the subject is in need of improvement in the subject's short-term memory.

* * * * *

SEQUENCE LISTING

```
<160> NUMBER OF SEQ ID NOS: 6

<210> SEQ ID NO 1
<211> LENGTH: 339
<212> TYPE: DNA
<213> ORGANISM: Mus musculus
<220> FEATURE:
<221> NAME/KEY: CDS
<222> LOCATION: (1)..(339)

<400> SEQUENCE: 1 cag gtc caa ctg cag cag cct ggg gct gaa ctg gtg aag cct ggg gcc      48
Gln Val Gln Leu Gln Gln Pro Gly Ala Glu Leu Val Lys Pro Gly Ala
1               5                   10                  15 tca gtg aag ctg tcc tgc aag gct tct ggc tac acc ttc acc agc ttc      96
Ser Val Lys Leu Ser Cys Lys Ala Ser Gly Tyr Thr Phe Thr Ser Phe
            20                  25                  30
```

| | | | | | | | | | | | | | | | | |
|---|---|---|---|---|---|---|---|---|---|---|---|---|---|---|---|---|
| tgg | atg | cac | tgg | gtg | att | cag | agg | cct | gga | caa | ggc | ctt | gag | tgg | att | 144 |
| Trp | Met | His | Trp | Val | Ile | Gln | Arg | Pro | Gly | Gln | Gly | Leu | Glu | Trp | Ile | |
| | | 35 | | | | | 40 | | | | | 45 | | | | |
| gga | gag | atg | aat | cct | agc | gac | ggt | cgt | act | cac | ttc | aat | gaa | aag | ttc | 192 |
| Gly | Glu | Met | Asn | Pro | Ser | Asp | Gly | Arg | Thr | His | Phe | Asn | Glu | Lys | Phe | |
| | 50 | | | | | 55 | | | | | 60 | | | | | |
| aag | acc | aag | gcc | aca | ctg | act | ata | gac | aca | tcc | tcc | aac | aca | gcc | tac | 240 |
| Lys | Thr | Lys | Ala | Thr | Leu | Thr | Ile | Asp | Thr | Ser | Ser | Asn | Thr | Ala | Tyr | |
| 65 | | | | | 70 | | | | | 75 | | | | | 80 | |
| atg | gaa | ctc | aac | agc | ctg | aca | tct | gag | gac | tct | gcg | gtc | tat | tac | tgt | 288 |
| Met | Glu | Leu | Asn | Ser | Leu | Thr | Ser | Glu | Asp | Ser | Ala | Val | Tyr | Tyr | Cys | |
| | | | | 85 | | | | | 90 | | | | | 95 | | |
| gca | aga | agg | atg | gag | gac | tgg | ggc | caa | ggg | act | ctg | gtc | act | gtt | tct | 336 |
| Ala | Arg | Arg | Met | Glu | Asp | Trp | Gly | Gln | Gly | Thr | Leu | Val | Thr | Val | Ser | |
| | | | 100 | | | | | 105 | | | | | 110 | | | |
| gca | | | | | | | | | | | | | | | | 339 |
| Ala | | | | | | | | | | | | | | | | |

<210> SEQ ID NO 2
<211> LENGTH: 113
<212> TYPE: PRT
<213> ORGANISM: Mus musculus

<400> SEQUENCE: 2

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Phe
            20                  25                  30

Trp Met His Trp Val Ile Gln Arg Pro Gly Gln Gly Leu Glu Trp Ile
        35                  40                  45

Gly Glu Met Asn Pro Ser Asp Gly Arg Thr His Phe Asn Glu Lys Phe
    50                  55                  60

Lys Thr Lys Ala Thr Leu Thr Ile Asp Thr Ser Ser Asn Thr Ala Tyr
65                  70                  75                  80

Met Glu Leu Asn Ser Leu Thr Ser Glu Asp Ser Ala Val Tyr Tyr Cys
                85                  90                  95

Ala Arg Arg Met Glu Asp Trp Gly Gln Gly Thr Leu Val Thr Val Ser
            100                 105                 110

Ala

<210> SEQ ID NO 3
<211> LENGTH: 324
<212> TYPE: DNA
<213> ORGANISM: Mus musculus
<220> FEATURE:
<221> NAME/KEY: CDS
<222> LOCATION: (1)..(324)

<400> SEQUENCE: 3

| | | | | | | | | | | | | | | | | |
|---|---|---|---|---|---|---|---|---|---|---|---|---|---|---|---|---|
| gac | atc | aag | atg | acc | cag | tct | cca | tct | tcc | atg | tat | gca | tct | cta | gga | 48 |
| Asp | Ile | Lys | Met | Thr | Gln | Ser | Pro | Ser | Ser | Met | Tyr | Ala | Ser | Leu | Gly | |
| 1 | | | | 5 | | | | | 10 | | | | | 15 | | |
| gag | aga | gtc | act | atc | act | tgc | aag | gcg | agt | cag | gac | att | aat | agc | tat | 96 |
| Glu | Arg | Val | Thr | Ile | Thr | Cys | Lys | Ala | Ser | Gln | Asp | Ile | Asn | Ser | Tyr | |
| | | | 20 | | | | | 25 | | | | | 30 | | | |
| tta | ggc | tgg | ttc | cag | cag | aaa | cca | ggg | aaa | tct | cct | aag | acc | ctg | ata | 144 |
| Leu | Gly | Trp | Phe | Gln | Gln | Lys | Pro | Gly | Lys | Ser | Pro | Lys | Thr | Leu | Ile | |
| | | 35 | | | | | 40 | | | | | 45 | | | | |
| tat | ggt | gca | aac | aga | ttg | gta | gat | ggg | gtc | cca | tca | agg | ttc | agt | ggc | 192 |

```
Tyr Gly Ala Asn Arg Leu Val Asp Gly Val Pro Ser Arg Phe Ser Gly
        50                  55                  60 agt gga tct ggg caa gat tac tct ctc acc atc agc agc ctg gag tat     240
Ser Gly Ser Gly Gln Asp Tyr Ser Leu Thr Ile Ser Ser Leu Glu Tyr
 65              70                  75                  80 gac gat atg gga ata tat tat tgt cta cag tat gat gag ttt ccg ctc     288
Asp Asp Met Gly Ile Tyr Tyr Cys Leu Gln Tyr Asp Glu Phe Pro Leu
                 85                  90                  95 acc ttc ggt gct ggg acc aag ctg gag ctg aaa cgg                     324
Thr Phe Gly Ala Gly Thr Lys Leu Glu Leu Lys Arg
                100                 105

<210> SEQ ID NO 4
<211> LENGTH: 108
<212> TYPE: PRT
<213> ORGANISM: Mus musculus

<400> SEQUENCE: 4

Asp Ile Lys Met Thr Gln Ser Pro Ser Ser Met Tyr Ala Ser Leu Gly
 1               5                  10                  15

Glu Arg Val Thr Ile Thr Cys Lys Ala Ser Gln Asp Ile Asn Ser Tyr
                20                  25                  30

Leu Gly Trp Phe Gln Gln Lys Pro Gly Lys Ser Pro Lys Thr Leu Ile
            35                  40                  45

Tyr Gly Ala Asn Arg Leu Val Asp Gly Val Pro Ser Arg Phe Ser Gly
        50                  55                  60

Ser Gly Ser Gly Gln Asp Tyr Ser Leu Thr Ile Ser Ser Leu Glu Tyr
 65              70                  75                  80

Asp Asp Met Gly Ile Tyr Tyr Cys Leu Gln Tyr Asp Glu Phe Pro Leu
                 85                  90                  95

Thr Phe Gly Ala Gly Thr Lys Leu Glu Leu Lys Arg
                100                 105

<210> SEQ ID NO 5
<211> LENGTH: 42
<212> TYPE: PRT
<213> ORGANISM: Homo sapiens

<400> SEQUENCE: 5

Tyr Ala Glu Gly Thr Phe Ile Ser Asp Tyr Ser Ile Ala Met Asp Lys
 1               5                  10                  15

Ile His Gln Gln Asp Phe Val Asn Trp Leu Leu Ala Gln Lys Gly Lys
                20                  25                  30

Lys Asn Asp Trp Lys His Asn Ile Thr Gln
            35                  40

<210> SEQ ID NO 6
<211> LENGTH: 13
<212> TYPE: PRT
<213> ORGANISM: Artificial Sequence
<220> FEATURE:
<223> OTHER INFORMATION: Synthetic sequence

<400> SEQUENCE: 6

Glu Met Asn Pro Ser Asp Gly Arg Thr His Phe Asn Glu
 1               5                  10
```